United States Patent [19]

Tsutsumi et al.

[11] Patent Number: 4,504,409
[45] Date of Patent: Mar. 12, 1985

[54] EMULSIFYING COMPOSITION

[75] Inventors: Hisao Tsutsumi, Miyashiro; Tomoko Inoue, Yokohama; Atsuo Ishida, Chiba, all of Japan

[73] Assignee: Kao Corporation, Tokyo, Japan

[21] Appl. No.: 443,611

[22] Filed: Nov. 22, 1982

[30] Foreign Application Priority Data

Dec. 16, 1981 [JP] Japan .................. 56-203189

[51] Int. Cl.³ .................................. C11D 3/36
[52] U.S. Cl. .................. 252/351; 252/174.16; 252/DIG. 17
[58] Field of Search .......... 252/351, 174.16, DIG. 17

[56] References Cited

U.S. PATENT DOCUMENTS 4,139,485  2/1979  Imokawa et al. .............. 252/174.16

OTHER PUBLICATIONS

Hackh's Chemical Dictionary, Fourth Edition, Julius Grant, pp. 205 and 240.

*Primary Examiner*—John Kight
*Assistant Examiner*—Marvin L. Moore
*Attorney, Agent, or Firm*—Oblon, Fisher, Spivak, McClelland & Maier

[57] ABSTRACT

Disclosed herein is an emulsifying composition which comprises one or more of the alkyl or alkenyl glyceryl ether phosphate compounds represented by the formula (I) and/or (II):

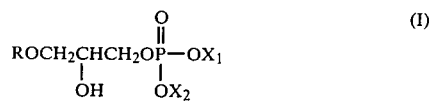

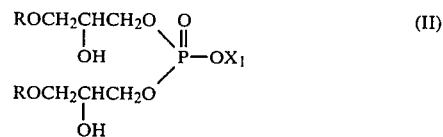

in which R represents a linear saturated or unsaturated hydrocarbon group having 8–20 carbon atoms, $X_1$ and $X_2$ are independently a pair ion selected from the group consisting of hydrogen, alkali metal, ammonium, alkylammonium which has an alkyl group having 1–5 carbon atoms, and alkanolamine which has a hydroxyalkyl group having 2 or 3 carbon atoms.

The above emulsifying composition is high in safety against skin and can be widely used in either type of W/O or O/W emulsion.

12 Claims, No Drawings

EMULSIFYING COMPOSITION

BACKGROUND OF THE INVENTION (i) Field of the Invention

This invention relates to emulsifying compositions and more particularly, to emulsifying compositions of the type which comprises alkyl or alkenyl glyceryl ether phosphates or salts thereof and which exhibits reduced irritativeness against living body and particularly skin and has the excellent emulsification stabilizing ability.

(ii) Description of the Prior Art

In general, compounds used as an emulsifier for emulsifying composition can broadly be classified into two categories including a hydrophilic emulsifier group which shows high solubility in water or has high HLB values and an oleophilic emulsifier group which shows high solubility in oil or has small HLB values. The hydrophilic emulsifier group has been utilized for stabilizing chiefly oil-in-water type (O/W type) emulsions while the oleophilic emulsifier group utilized for stabilizing water-in-oil type (W/O type) emulsions. In this connection, however, oils greatly differ in property depending on the type of oil and thus an HLB value required for the emulsification depends on the type of an oil to be emulsified. Accordingly, it is general that hydrophilic emulsifiers and oleophilic emulsifiers are hardly employed singly, but both the emulsifiers are mixed to properly adjust the HLB value for emulsification. This is true especially when oils to be emulsified are in mixed form.

Conventionally employed hydrophilic emulsifiers are, for example, anionic surface active agents such as alkali metal salts of fatty acids, alkylsulfates and the like, ethylene oxide-added nonionic active agents such as polyoxyethylene alkyl ethers, polyoxyethylene-fatty acid esters, polyoxyethylene sorbitan-fatty acid esters and the like. On the other hand, oleophilic emulsifiers are, for example, nonionic surface active agents such as sorbitan-fatty acid esters, glycerine-fatty acid esters and the like.

Emulsifier compositions which are obtained by mixing hydrophilic emulsifiers, which are combinations of fatty acid-triethanolamine salts and ethylene oxide-added nonionic surface active agents with oleophilic emulsifiers such as glycerine-fatty acid esters to have various levels of HLB values are very stable in emulsification stability, so that they have widely utilized in the field of cosmetics such as creams.

However, it is suggested that ethylene oxide addition-type nonionic surface active agents contain formalin, dioxane and the like as impurities and these impurities have the allergic action on living body. In addition, it is known that anionic surface active agents generally produce high skin irritation and are thus not favored as an emulsifier. Accordingly, it is the common practice to use as the anionic surface active agent alkali metal salts of fatty acids which produce relatively low skin irritation, with the attendant disadvantage that the resulting emulsion becomes alkaline in nature.

On the other hand, it is known that there are present in the living body a group of compounds called phospholipids which possess surface active properties and that they play a very important role as the main components of membranes of the living body. Typical examples of the phospholipid include glycerophospholipids such as phosphatidyl choline (lecithin), phosphatidyl ethanolamine (cephalin), phosphatidyl serine and the like. These phospholipids are components in vivo and are surface active materials which are highly safe for use on the living body. For instance, lecithin has been industrially utilized as an emulsifier. However, these are of natural origin and have various impurities and suffer deterioration in quality inherent of natural materials with the passage of time. Furthermore, the structure such as that of a fatty acid composition cannot be arbitrarily changed, so that its HLB value cannot also be changed freely with unsatifactory emulsifying activity. Thus, they are not satisfactory for use as an emulsifier and have limitations in application.

SUMMARY OF THE INVENTION

We have made an intensive study to develop emulsifying compositions which are highly safe for the living body and also have a good emulsification stability. As a result, it has been found the above object can be achieved by using alkyl or alkenyl glyceryl ether phosphate compounds represented by the general formula (I) and/or (II)

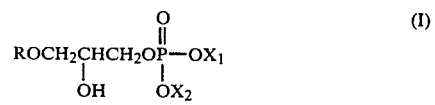

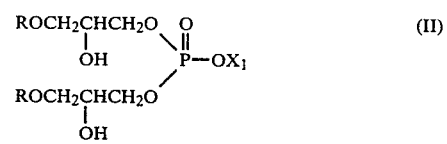

in which all R may be the same or different and represent a linear saturated or unsaturated hydrocarbon group having 8–20 carbon atoms, $X_1$ and $X_2$ are independently a pair ion selected from the group consisting of hydrogen, alkali metal, ammonium, alkylammonium which has an alkyl group having 1–5 carbon atoms, and alkanolamine which has a hydroxyalkyl group having 2 or 3 carbon atoms.

That is, the present invention provides emulsifying compositions which comprise one or more of the alkyl or alkenyl glyceryl ether phosphate compounds represented by the general formula (I) and/or (II).

DETAILED DESCRIPTION OF THE INVENTION AND PREFERRED EMBODIMENTS

The method of preparing the alkyl or alkenyl glyceryl ether phosphate compounds of the general formula (I) and/or (II) is not to critical and, for example, alkyl or alkenyl glycidyl ethers are reacted with phosphoric acid according to the following reaction formula

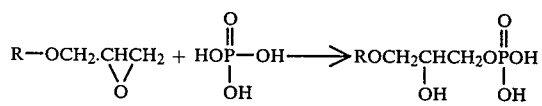

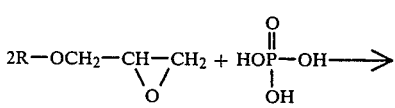

-continued

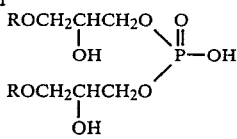

The resulting alkyl or alkenyl glyceryl ether phosphates are, if necessary, neutralized with appropriate alkali agents. The salts may be formed by separately adding the phosphates and an alkali agent in the compounding vessel for neutralization or adjustment of the pH. In a preferred aspect, a nascent emulsification method is used in which the phosphate is added in the form of an acid at the time when an emulsion is prepared, and the emulsification is effected while adding an alkali agent.

Typical phosphate compounds obtained by the above preparation method are indicated below along with their properties shown in Table 1.

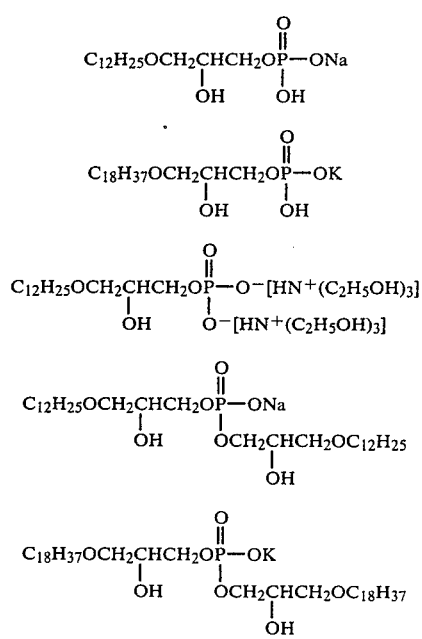

TABLE 1

| Sample | a | b | c | d | e |
|---|---|---|---|---|---|
| Appearance | White Powder | White Powder | White Powder | White Powder | White Powder |
| Odor | Little | Little | Little | Little | Little |
| Solubility in Water | | | | | |
| (25° C.) | Good | Insoluble (gel form) | Good | Insoluble | Insoluble |
| (70° C.) | Good | Good | Good | Good | Good |
| pH (1%) | 5.3 | 6.5 | 7.6 | 6.4 | 5.8 |

The emulsifying composition comprising the alkyl or alkenyl glyceryl ether phosphate compounds of the invention is high in safety against skin and can be adjusted to a desired level of HLB when oleophilic emulsifiers are used in combination, so that oily components can be kept in the system in a wide range of amounts, coupled with another advantage that it can be widely used in either type of W/O or O/W.

The emulsifying composition of the invention has such a widely applicable stabilizing effect as mentioned above, so that it has wide utility not only in the fields of the medical, cosmetic and food industries, but also almost all the fields of the fiber, metal, agricultural and synthetic resin industries. Above all, the composition can suitably be used in the technical field of cosmetics and medicines which relate to products directly applicable to the skin. Therefore, an embodiment in the field of cosmetics is particularly described.

In the field of cosmetics and allied articles, safety against skin is first required and accordingly, suitable selection of the pair ion of the alkyl or alkenyl glyceryl ether phosphate compounds is necessary. That is, if the pair ions $X_1$ and $X_2$ of the alkyl or alkenyl glyceryl ether phosphate compound represented by the general formula (I) and/or (II) are both hydrogen, its acidity becomes too high, whereas if both are an alkali metal, the alkalinity becomes too high. Accordingly, both ion pairs should not be hydrogen or an alkali metal. This control can be achieved by adjusting the pH in the range of 4–9, preferably 5–7.

The pair ion species should preferably be sodium, potassium, triethanolammonium, ammonium and hydrogen.

Among various alkyl or alkenyl glyceryl ether phosphate compounds represented by the general formula (I) and/or (II), alkyl glyceryl ether phosphates are preferable.

The hydrocarbon group R of the alkyl glyceryl ether phosphate compound should favorably be an alkyl group having 12–18 carbon atoms.

The alkyl glyceryl ether phosphate compounds of the general formulas (I) and (II) may be used singly or in combination at arbitrary ratios depending on the type of an oil to be emusified (and if mixed, the weight ratio of the general formula (I)/the general formula (II) is preferably 100/0–20/80). If necessary, the compound may be used by mixing with oleophilic emulsifiers at arbitrary ratios.

The oleophilic emulsifiers used are not critically limited but those containing ethylene oxide groups are preferable and include, for example, sorbitan-fatty acid esters, glycerine-fatty acid esters, sucrose-fatty acid esters, propylene glycol-fatty acid esters and the like in the form of mono- or diesters whose fatty acid moiety has 10 to 20 carbon atoms. These esters are used singly or in combination.

Emulsified cosmetics using the emulsifier of the present invention can be prepared by compounding, according to the usual manner, the emulsifier and known cosmetic ingredients such as, for example, cosmetic oily substrates, surface active agents, viscosity modifiers, medical ingredients, preservatives and other wetting agents.

Examples of the cosmetic oily substrate include hydrocarbons such as liquid paraffin, paraffin wax, ceresine, squalane and the like; waxes such as bees wax, spermaceti, carnauba wax and the like; natural animal and plant oils and fats such as olive oil, tsubaki oil, jojoba oil, lanolin and the like; and silicone oils, fatty acids, higher alcohols and ester oils obtained by reaction of these acids and alcohols. As surface active agents there are mentioned polyoxyethylene alkyl ethers, polyoxyethylene-fatty acid esters, polyoxyethylene sorbitan fatty acid esters, polyoxyethylene sorbital fatty acid esters, polyoxyethylene hardened castor oils, alkylsulfates, polyoxyethylene alkylsulfates, alkylphosphates, polyoxyethylene alkylphosphates, alkali metal salts of fatty acids and the like. These agents can be added to an extent not impeding the effect of the present invention. Moreover, examples of the viscosity modifier include high molecular weight compounds such as polyvinyl alcohol, carboxyvinyl polymer, carboxymethyl cellulose, polyvinylpyrrolidone, hydroxyethyl cellulose, methyl cellulose and the like; natural gum such as gelatin, tragacanth gum and the like; and alcohols such as ethanol, isopropanol and the like. The medical ingredients are bactericides, antiphlogistics, vitamins and the like and the wetting agents include propylene glycol, glycerine, 1,3-butylene glycol, sorbitol, lactic acid, sodium lactate, sodium pyrrolidonecarbonate and the like. The preservatives include, for example, paraoxybenzoates, benzoic acid, sodium benzoate, sorbic acid, potassium sorbate, phenoxyehtanol and the like.

Preferred compositions of an emulsified cosmetic according to one embodiment of the present invention are as follows.

|  | Compounding Amount (wt %) | Preferable Compounding Amount (wt %) |
|---|---|---|
| Cosmetic oil substrate | 1–60 | 5–35 |
| Emulsifier | 0.1–10 | 0.5–7 |
| Viscosity modifier, etc. | 0–10 | 0–5 |
| Medical agent | 0–10 |  |
| Wetting agent | 0–30 | 0–10 |
| Preservative | 0–1 | 0.02–1.0 |
| Water | 25–95 | 40–90 |

The emulsifier may be separately prepared or the starting materials for the emulsifier may be directly charged into the cosmetic compounding composition.

The emulsified cosmetics can be prepared in various forms including, for example, vanishing creams, lotions, cold creams, cleansing creams, hair creams, foundation creams, hand creams and the like. They can be in either of emulsification type, O/W or W/O.

The thus obtained emulsified cosmetics which are one of embodiments of the present invention exhibit excellent stability of emulsification and excellent skin-protecting effect and have excellent feeding to the touch.

The present invention is particularly described by way of a synthetic example and examples.

SYNTHETIC EXAMPLE

Into a 1 liter round bottom flask equipped with a reflux condenser, thermometer, dropping funnel and agitator were charged 277 g (2.8 moles) of 99% orthophosphoric acid and 250 ml of diethyl ether. Into the mixture was dropped 231 g of lauryl glycidyl ether (oxirane value 225.8, 0.93 mole) in 1 hour while refluxing the diethyl ether (35°–40° C.). After completion of the dropping, the agitation was continued under heating conditions of 35°–40° C. for further 3 hours. After completion of the reaction, 500 ml of diethyl ether and 500 ml of 1N hydrochloric acid were added to the reaction mixture and mixed together. The thus obtained mixed solution was transferred to a separating funnel and shaked to extract unreacted phosphoric acid in the acidic aqueous phase of hydrochloric acid. The organic phase was separated and washed with 500 ml of 1/10N hydrochloric acid, after which the solvent was distilled off under reduced pressure to obtain 410 g of a mixture of a phosphate and a nonionic substance.

Then, the mixture was neutralized with an ethanol solution of potassium hydroxide to precipitate the phosphate component as the potassium salt. After removal of the ethanol by distillation, the remaining white precipitate was reduced into pieces and washed several times with 500 ml of hot acetone to remove the nonionic substance therefrom. Thereafter, the solid was removed by filtration and dried under reduced pressure to obtain 328 g of the potassium salt of the phosphate.

The potassium salt was dissolved in 1 liter of 6N hydrochloric acid and was thus made acidic. The resulting phosphate was extracted with 500 ml of diethyl ether and the organic phase was washed with 500 ml of 1/10N hydrochloric acid, after which the solvent was distilled off under reduced pressure to obtain 275 g of the purified phosphate. The acid value of the phosphate (mg of potassium hydroxide required for neutralization of 1 g of sample to the first equivalence point $=AV_1=151.0$, mg of potassium hydroxide required for the second equivalence point $=AV_2=302.6$) revealed that a monophosphate was obtained. The yield was found to be 80% (based on the glycidyl ether, with a water content of 8%).

This compound was confirmed to be composed of a phosphorus compound alone when determined by a procedure comprising, after methyl esterification with diazomethane, trimethylsilylation with BSTFA (N,O-bis-trimethylsilyltrifluoroacetamide) and subjecting the resulting compound to the gas chromatography (flame photometer and hydrogen flame ionization detector).

Moreover, when the phosphate compound was trimethylsilylated with BSTFA and its CI mass spectrum was observed, the molecular weight at the parent peak (m/e=556) was coincident as the trimethylsilylated phosphate compound.

The elementary analysis was effected as follows: the purified phosphate was again dissolved in an ethanol solution of potassium hydroxide to give a dipotassium salt and the salt was separated by filtration and dried under reduced pressure.

Elementary Analysis $C_{15}H_{31}O_6PK_2$: Calculated: C: 43.2, H: 7.5, P: 7.4, K: 18.8, Found: C: 43.5, H: 7.9, P: 7.1, K: 18.0.

$^1$HNMR (CDCl$_3$, Internal Standard: tetramethylsilane (TMS)): $\delta 0.87$ ppm (t, 3H, —CH$_3$); $\delta 1.27$ ppm (broad s, 20H, —(CH$_2$—)$_{10}$); $\delta 3.26 \sim 4.\overline{27}$ ppm (broad, 7H,

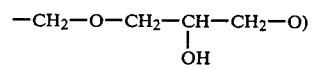

$^{13}$CNMR (CDCl$_3$, Internal standard TMS):

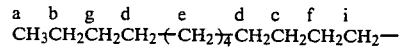

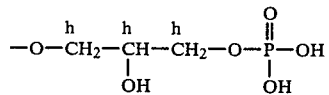

$\delta$(ppm): a: 14.1, b: 22.7, c: 26.2, d: 29.5, e: 29.8, f: 29.8, g: 32.0, h: 66.6~71.0, i: 72.0

IR (film) 3300, 2900, 2840, 1460, 1000 cm$^{-1}$.

EXAMPLE 1

A 10% aqueous solution of each of the compounds (a)–(e) of the present invention and four comparative products was subjected to the close patch test using a total of three groups of guinea pigs, each consisting of 6 guinea pigs, for 24 hours. After removal of the patch, the intensity of the skin reaction after 24 hours was evaluated in seven steps including redness (±, +, ++), chemosis (±, +, ++) and negative (−). "−", "±", "+" and "++" were scored as 0, 0.5, 1.0 and 2.0, respectively, and a total score of the redness and chemosis was determined, from which an average value of 6 guinea pigs was obtained as an average stimulative value for comparing intensities of the skin stimulativeness with one another. The results are shown in Table 2.

TABLE 2

| | Sample | Average Stimulative Value | Other Skin Reaction |
|---|---|---|---|
| Compound of the present Invention | a | 0.4 | Same as water |
| | b | 0 | Same as water |
| | c | 0.4 | Same as water |
| | d | 0.2 | Same as water |
| | e | 0 | Same as water |
| Comparative product | Sodium laurylsulfate | 3.2 | Heavy falling-off waste |
| | Sodium dodecylbenzenesulfonate | 2.0 | Moderate falling-off waste |
| | Sodium alpha-dodecenesulfonate | 0.7 | Slight falling-off waste |
| | Sodium lauryl polyoxyethylene sulfate | 0.9 | Slight gloss |

As will be apparent from the above results, the known anionic active agents which have been utilized as the hydrophilic emulsifier have a substantial degree of skin stimulativeness but the compounds of the present invention have a much reduced degree of stimulativeness.

EXAMPLE 2

An O/W type emulsifier of the following composition was prepared to determine the pH and the day-by-day stability of the emulsifier.

| Test oil (olive oil) | 25 wt % |
|---|---|
| Test emulsifier | 4 |
| Water | 71 |

The emulsifier was made by a phase invention emulsification method in which the test oil and the test emulsifier were mixed together and heated to 70° C., to which was gradually added water of 70° C. under agitation. It will be noted that as described in the results of Table 3, in some of the experiments, a so-called nascent emulsification method was used in which non-neutralized test emulsifiers were mixed with test oils, to which was added an aqueous solution of an alkali agent to be a pair ion so that the neutralization was effected while emulsifying. The resulting emulsions were allowed to stand at 20° C. and 40° C. for 1 month and their stability was evaluated according to the following standard.

Standard of Judging the Stability (−): No separation
(+): Slight separation of oil component
(++): Separation into two phases of cream phase and drainage phase
(+++): Separation into three phases including cream phase, drainage phase and combined phase.
(++++): Disappearance of cream phase and separation into two phases including oil phase and aqueous phase.

TABLE 3

| | Test Emulsifier | pH | Stability 20° C. | Stability 40° C. |
|---|---|---|---|---|
| Compound of the present Invention | Mixture of compound (a) of Table 1 and monoglyceride stearate (mixing ratio 1/1)* | 6.5 | — | — |
| | Mixture of compound (a) of Table 1 compound (d) of Table 1 (mixing ratio 1/1) | 6.4 6.4 | — | — |
| | Mixture of compound (b) of Table 1 and monoglyceride stearate (mixing ratio 1/1)* | 6.6 | — | — |
| Comparative Product | Mixture of triethanolamine stearate monoglyceride stearate (mixing ratio 1/1)* | 8.2 | — | + |
| | Mixture of polyoxyethylene (20) sorbitan monostearate and monoglyceride stearate (mixing ratio 1/1) | 6.3 | +++ | +++ |
| | Mixture of polyoxyethylene(20) oleyl ether and monoglyceride stearate (mixing ratio 1/1) | 6.0 | +++ | +++ |
| | Mixture of potassium myristate and monoglyceride stearate (mixing ratio 1/1) | 8.5 | ++ | +++ |

*Emulsification by the nascent emulsification method

As the result of the test, it was found that the alkyl glyceryl ether phosphates to be the compounds of the invention had the excellent emulsifying ability as a hydrophilic emulsifier and that they had an emulsifying force equal to or higher than alkali metal salts of fatty acids and ethylene oxide-added nonionic active agents conventionally employed for the same purpose and served to render the emulsion weakly acidic.

As will be apparent from Examples 1 and 2, the use of the alkyl glyceryl ether phosphates which are the compounds of the present inventon makes it possible to readily manufacture emulsions of higher safety.

EXAMPLE 3

Hand Cream (O/W Type)

| 1. Non-neutralized product of (a) compound in Table 1 | 1.9 (%) |
|---|---|
| 2. Monoglyceride stearate | 1.5 |
| 3. Stearic acid | 8.0 |
| 4. Squalane | 4.0 |
| 5. Stearyl alcohol | 1.5 |
| 6. Butyl paraoxybenzoate | 0.1 |
| 7. Methyl paraoxybenzoate | 0.1 |
| 8. Dipropylene glycol | 5.0 |
| 9. Sodium hydroxide | 0.1 |
| 10. Perfume | 0.1 |
| 11. Purified water | balance |

1–6 were heated 70° C. and mixed together. Separately, a mixture of 7, 8, 9 and 11 was heated to 70° C. and was gradually added to the mixture of 1–6 for emulsification. Finally, 10 was added to the emulsion and well mixed, followed by cooling and charging into a container.

EXAMPLE 4

Cleansing Cream (O/W Type)

| 1. Compound (b) in Table 1 | 2.8 (%) |
|---|---|
| 2. Sorbitan sesquioleate | 2.2 |
| 3. Liquid paraffin | 25.0 |

| | -continued | |
|---|---|---|
| 4. | Octyldodecyl myristate | 15.0 |
| 5. | Cetanol | 2.0 |
| 6. | Bees wax | 1.0 |
| 7. | Ceresine wax | 1.5 |
| 8. | Propyl paraoxybenzoate | 0.2 |
| 9. | Propylene glycol | 5.0 |
| 10. | 1,3-butanediol | 5.0 |
| 11. | Perfume | 0.1 |
| 12. | Purified water | balance |

1–8 were heated to 70° C. and mixed. Separately, a mixture of 9, 10 and 12 were heated to 70° C. and gradually added to the mixture of 1–8 for emulsification. Finally, 11 was added to and mixed with the mixture, followed by cooling and charging into a container.

What is claimed is:

1. An emulsifying composition comprising one or more of alkyl or alkenyl glyceryl ether phosphates represented by the general formula (I) and/or (II)

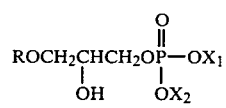

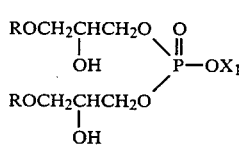

in which R may be the same or different and represent a linear saturated or unsaturated hydrocarbon group having 8–20 carbon atoms, $X_1$ and $X_2$ indepdently represent an ion pair selected from the group consisting of hydrogen, alkali metal, ammonium, alkylammonium having an alkyl group containing 1–5 carbon atoms, and alkanolamine having a hydroxyalkyl group which has 2 or 3 carbon atoms.

2. The emulsifying composition of claim 1 wherein one of the glyceryl ether phosphates has the formula:

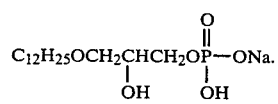

3. The emulsifying composition of claim 1 wherein one of the glyceryl ether phosphates has the formula:

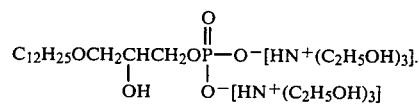

4. The emulsifying composition of claim 1 wherein one of the glyceryl ether phosphates has the formula:

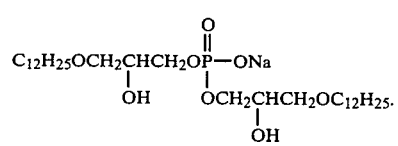

5. The emulsifying composition of claim 1 wherein one of the glyceryl ether phosphates has the formula:

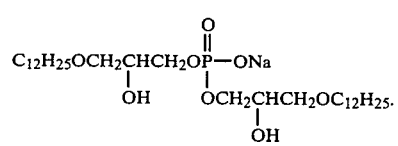

6. The emulsifying composition of claim 1 wherein one of the glyceryl ether phosphates has the formula:

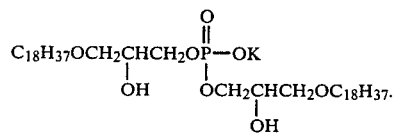

7. The emulsifying composition of claim 1, having a pH in water of between 4 and 9.

8. The emulsifying composition composition of claim 7, having a pH in water of between 5 and 7.

9. The emulsifying composition of claim 7, wherein $X_1$ and $X_2$ are selected from the group consisting of sodium, potassium, triethanol ammonium, ammonium and hydrogen, with the proviso that both are not sodium, potassium or hydrogen.

10. The emulsifying composition of claim 1, wherein R is a saturated $C_{12}$–$C_{18}$ hydrocarbon.

11. The emulsifying composition of claim 1, wherein the weight ratio of the formula (I) compounds to the formula ((II)) compounds is 100/0 to 20/80.

12. The emulsifying composition of claim 1, further comprising an oleophilic emulsifier selected from the group consisting of sorbittan-fatty acid esters, glycerine-fatty acids esters, sucrose-fatty acid esters poly propylene glycol-fatty acid esters in the form of mono or diesters of $C_{10}$–$C_{20}$ fatty acids, and mixtures thereof.

* * * * *